(12) United States Patent
Herold et al.

(10) Patent No.: US 7,738,624 B2
(45) Date of Patent: Jun. 15, 2010

(54) ADJUSTABLE PHANTOM

(75) Inventors: Mark D. Herold, Stow, OH (US); David D. Salk, Parma, OH (US); Adam S. Elkurd, Akron, OH (US); Kristin A. Babroski, Parma, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 59 days.

(21) Appl. No.: 12/159,793

(22) PCT Filed: Dec. 28, 2006

(86) PCT No.: PCT/US2006/062648
§ 371 (c)(1),
(2), (4) Date: Jul. 1, 2008

(87) PCT Pub. No.: WO2007/081662
PCT Pub. Date: Jul. 19, 2007

(65) Prior Publication Data
US 2009/0052755 A1  Feb. 26, 2009

Related U.S. Application Data

(60) Provisional application No. 60/766,259, filed on Jan. 5, 2006.

(51) Int. Cl.
*A61B 6/03* (2006.01)
*G01D 18/00* (2006.01)
(52) U.S. Cl. .................. 378/18; 378/204; 378/207

(58) Field of Classification Search .............. 378/18, 378/207, 204
See application file for complete search history.

(56) References Cited

U.S. PATENT DOCUMENTS

| | | | |
|---|---|---|---|
| 4,873,707 A | 10/1989 | Robertson | |
| 4,922,915 A * | 5/1990 | Arnold et al. | 382/128 |
| 4,985,906 A | 1/1991 | Arnold | |
| 6,148,057 A | 11/2000 | Urchuk et al. | |
| 6,225,622 B1 * | 5/2001 | Navarro | 250/252.1 |
| 6,493,574 B1 * | 12/2002 | Ehnholm et al. | 600/429 |
| 6,516,045 B2 * | 2/2003 | Shepherd et al. | 378/53 |
| 6,715,918 B2 * | 4/2004 | Mitschke et al. | 378/207 |
| 6,843,145 B2 * | 1/2005 | Jaszczak et al. | 73/866.4 |
| 6,932,506 B2 * | 8/2005 | Mitschke et al. | 378/207 |

(Continued)

FOREIGN PATENT DOCUMENTS

EP    0514971 A1    11/1992

(Continued)

OTHER PUBLICATIONS

Engdahl, T.; RC servo controlling; May 28, 2002, 2 pages, ELH Communications, Ltd.

(Continued)

*Primary Examiner*—Allen C. Ho

(57) ABSTRACT

An adjustable phantom (36) includes a base (202), an actuator (204) and a phantom (210). The phantom includes first (210*a*) and second portions (210*b*), each having a different value of a physical characteristic measured by a scanner (10). The phantom (210) is movable with respect to the base (202). In one embodiment, the phantom is well suited to simulating the arrival of contrast agent in a contrast enhanced imaging examination.

30 Claims, 7 Drawing Sheets

U.S. PATENT DOCUMENTS

Figure 1:
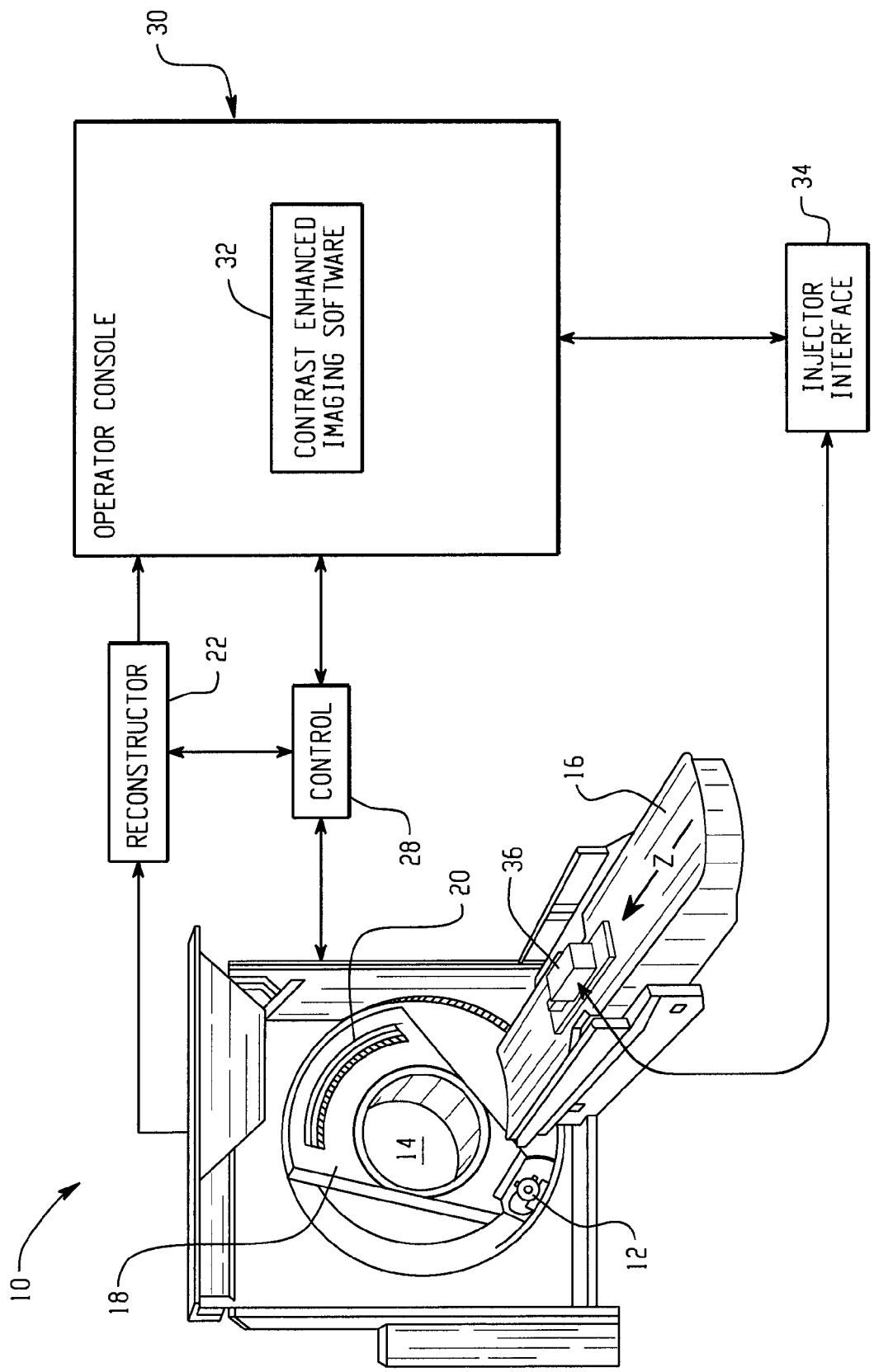

| | | | |
|---|---|---|---|
| 7,056,019 B1 * | 6/2006 | Hanson et al. | 378/207 |
| 7,151,253 B2 * | 12/2006 | Varchena et al. | 250/252.1 |
| 7,402,819 B2 * | 7/2008 | Saracen | 250/492.1 |
| 2002/0015476 A1 | 2/2002 | Reinwand et al. | |
| 2003/0072417 A1 | 4/2003 | Kaufhold et al. | |
| 2005/0002495 A1 | 1/2005 | Hein et al. | |

FOREIGN PATENT DOCUMENTS

| | | | |
|---|---|---|---|
| JP | 07080089 A | 3/1995 | |
| WO | 2004096047 A2 | 11/2004 | |

OTHER PUBLICATIONS

Griesser, D.; Intro to RC Servos; 200-2004, 9 pages.

Philips Medical Systems (Cleveland), iNC.; Brilliance CT Instruction for Use; 2005, 19 pages; Sec. 10-Bolus tracking.

* cited by examiner

ADJUSTABLE PHANTOM

The present invention relates to apparatus and methods for simulating the operation of medical imaging equipment such as computed tomography (CT) scanners, and particularly to testing and simulation in contrast enhanced imaging and angiography. It is also useful in other applications where it is desirable to simulate the change in contrast of an object as a function of time.

In contrast enhanced imaging, a contrast agent is introduced into the anatomy of a patient, typically by way of an intravenous or intra-arterial injection. Following a delay which allows the contrast agent to reach a region of interest (ROI) of the patient's anatomy, a scan of the region is initiated. Timing of scan is coordinated to coincide with the presence of the contrast agent at the ROI, as scanning either too early or too late can result in less than optimal enhancement, and possibly require that the patient be rescanned.

Various techniques for coordinating contrast enhanced scans have been implemented. These techniques typically include an optional surview scan which is used to determine the axial location of the ROI. In one technique, contrast is injected into the patient and a scan of the ROI is initiated after a predefined delay. However, the time delay for the contrast agent to reach the ROI varies from patient to patient, and the time delay for a particular patient can also vary from one scan to the next.

In another technique, a locator scan is obtained and used to identify one or more tracking ROIs. Contrast is then injected, and a series of low dose scans are obtained at the axial location. When the contrast agent is detected at the tracking ROI(s) at a desired enhancement level, a diagnostic scan is automatically triggered.

In a test injection method, the desired axial location is scanned and one or more tracking ROIs are identified. A relatively small amount of contrast is injected, and a series of low dose axial scans are obtained. Information from the test scan is used to calculate a scan delay. Contrast is then injected using a desired injection protocol, and a diagnostic scan is initiated after the calculated delay.

Application software which performs one or more of these techniques typically resides on a console or workstation associated with a CT scanner. One example of such commercially available software for use in CT imaging is the Bolus Pro software available from Philips Medical Systems.

In some situations, it is desirable to test or simulate the operation of a particular scanner together with the software with which it is used. For example, users can benefit from training which more accurately reflects actual operating conditions. Similarly, repeated testing of a scanner and/or its software under a variety of operating states or conditions as part of the design process can lead to a more robust design. It may also be desirable to test the scanner as part of the manufacturing process to assure that the scanner and its software are operating properly.

In the past, such testing and simulation has been difficult to perform. For example, a human tester has manually pulled a piece of contrast material through a scanner's examination region using a string. As will be appreciated, however, such manual testing has proven to be time consuming and relatively non-repeatable, and has required that the tester be in the vicinity of an operating scanner. Such a procedure is also poorly suited for use in training situations. Accordingly, there remains room for improvement.

Aspects of the present invention address these matters, and others.

According to a first aspect of the invention, an apparatus includes a base adapted to be placed on the object support of a scanner which generates information indicative of a physical characteristic of the interior of an object under examination, and a phantom carried by and movable with respect to the base in a direction of motion. The physical characteristic of the phantom varies along the direction of motion. The apparatus also includes an actuator which causes the phantom to move with respect to the base in the direction of motion.

According to another aspect of the invention, a method includes the steps of positioning a phantom with respect to the object support of a medical imaging scanner, which scanner generates information indicative of a physical characteristic of the interior of an object under examination, using an actuator to move the phantom relative to the object support so as to change the value of the physical characteristic in a region of interest, scanning the region of interest, repeating the step of scanning a plurality of times during movement of the phantom, and using information from the scans to determine the value of the physical characteristic in the region of interest at a plurality of times.

According to another aspect of the invention, an apparatus includes a base adapted to be placed in the examination region of a scanner which generates information indicative of a physical characteristic of the interior of an object under examination, a phantom carried by and movable with respect to the base in a direction of motion, and an actuator which causes the phantom to move with respect to the base in the direction of motion so as to vary the value of the physical characteristic in a region of interest. The phantom includes a first portion in which the physical characteristic has a first value and a second portion in which the physical characteristic has a second value.

Those skilled in the art will appreciate still other aspects of the present invention upon reading an understanding the attached figures and description.

Figure 2:
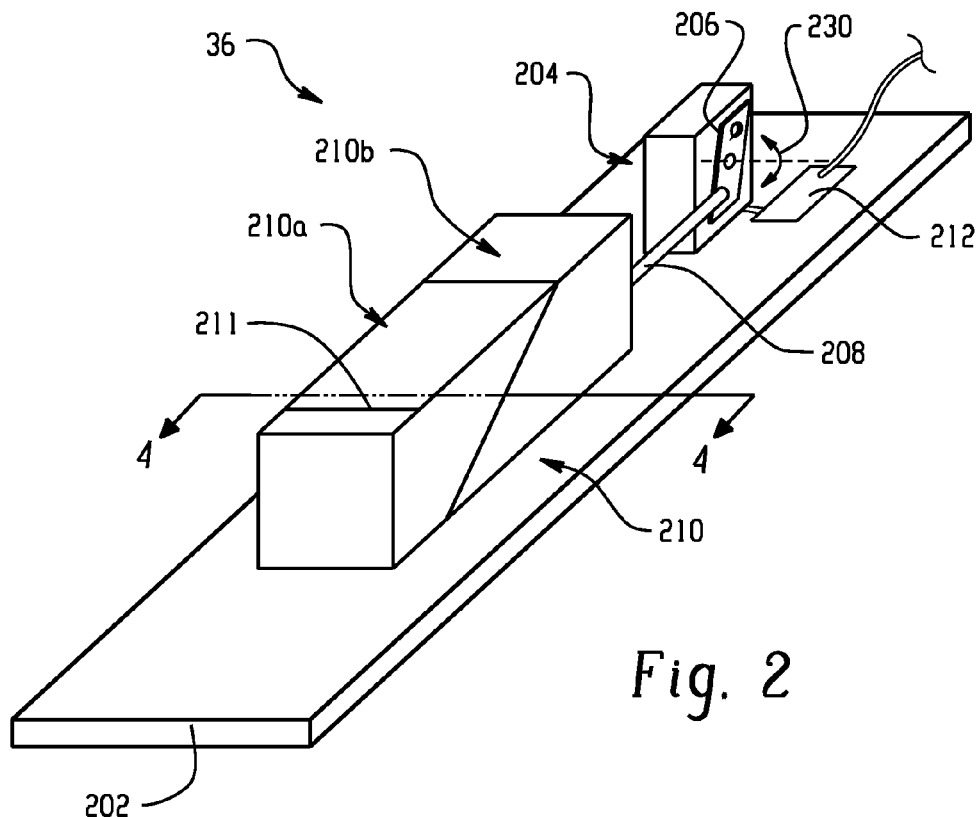
Figure 3A:
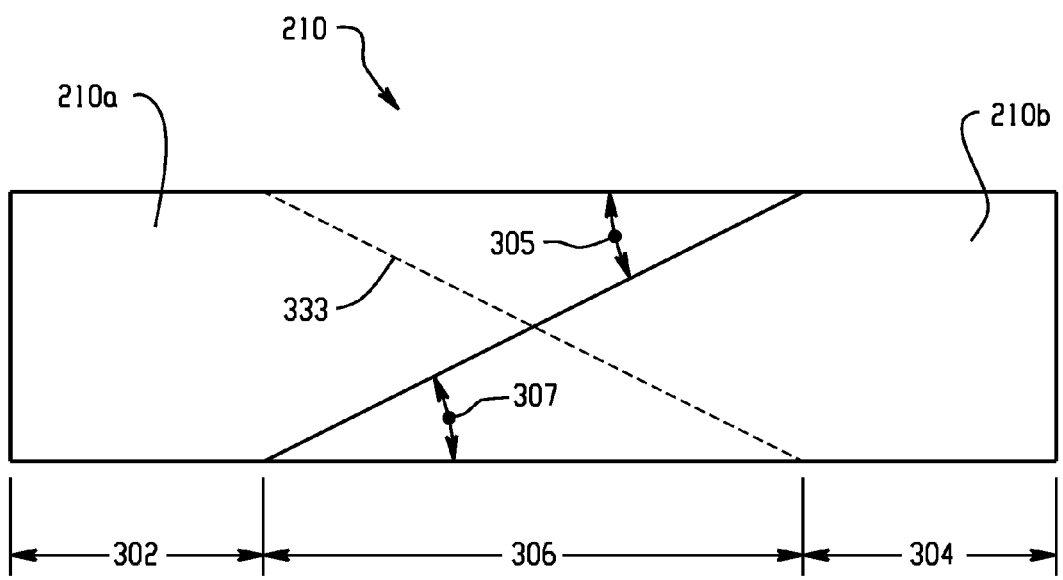
Figure 4:
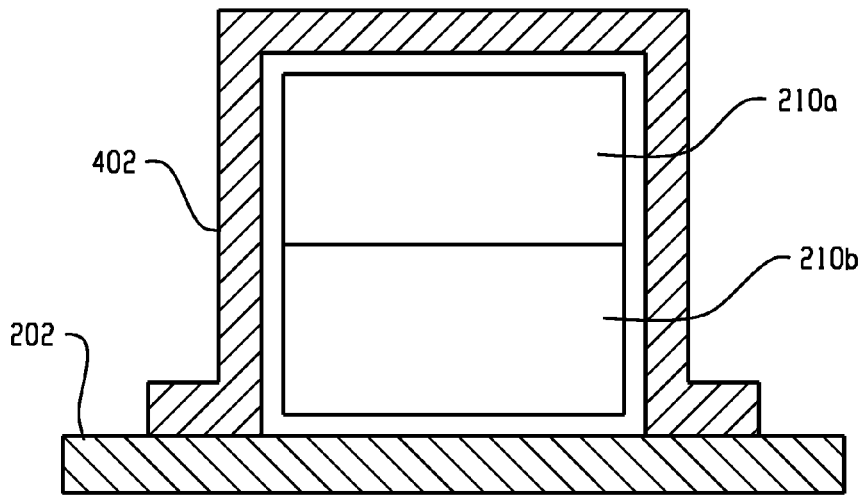
Figure 5:
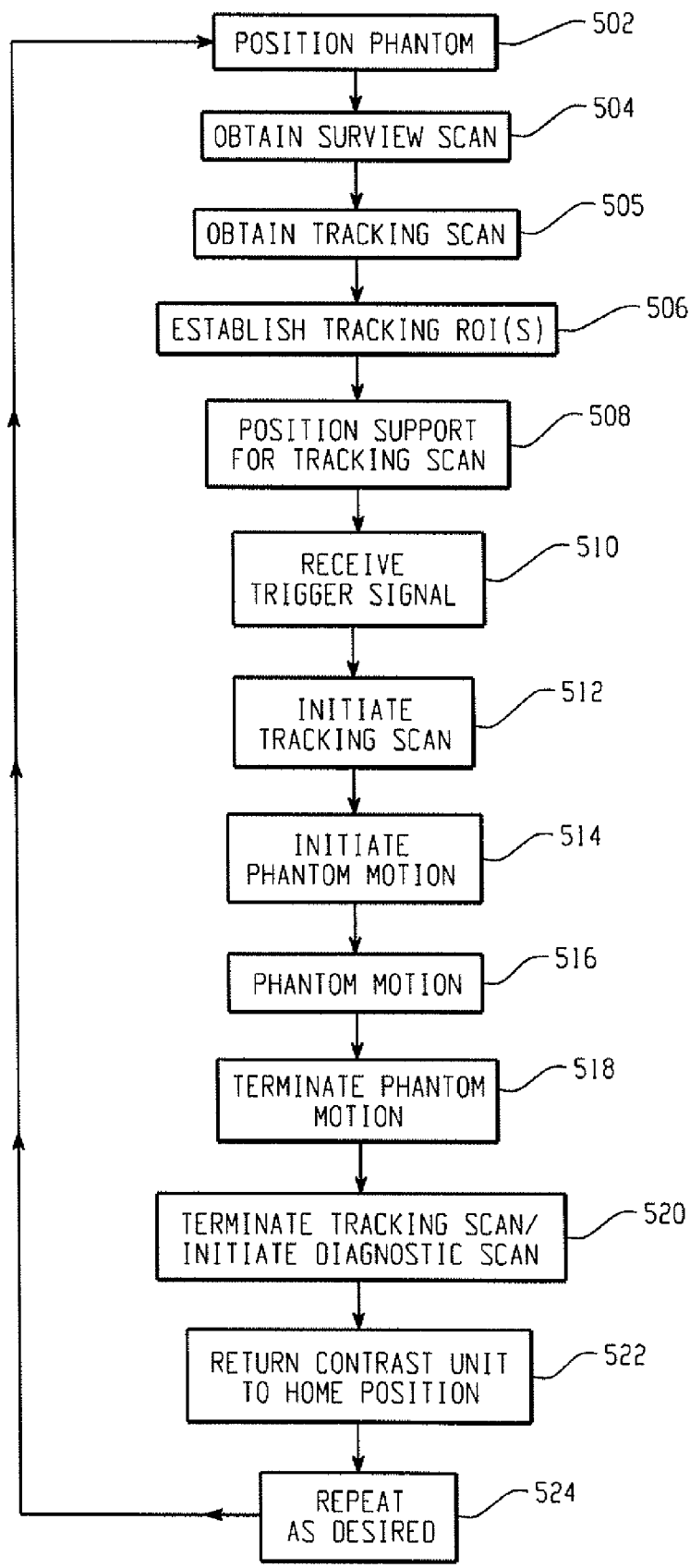
Figure 6:
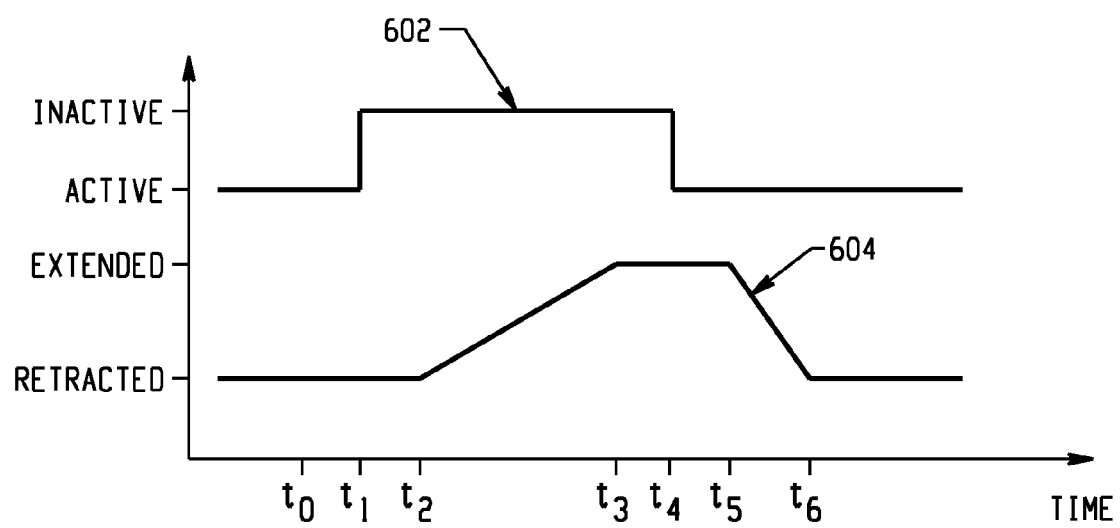

The present invention is illustrated by way of example and not limitation in the figures of the accompanying drawings, in which like references indicate similar elements and in which:

FIG. 1 depicts at CT scanner and phantom.
FIG. 2 is a perspective view of a phantom.
FIGS. 3a, 3b, 3c, and 3d are side views of phantom.
FIG. 4 is a transverse cross section of the phantom.
FIG. 5 depicts a simulated tracking scan.
FIG. 6 is a timing diagram of a tracking scan.
FIGS. 7a, 7b, 7c, and 7d present an end view of a phantom with tracking ROIs depicted thereon.

With reference to FIG. 1, a CT scanner 10 includes a rotating gantry 18 which rotates about the z-axis. The gantry 18 supports an x-ray source 12 such as an x-ray tube. The gantry 18 also supports an x-ray sensitive detector 20 which subtends an angular arc on the opposite side of an examination region 14. X-rays produced by the x-ray source 12 traverse the examination region 14 and are detected by the detector 20.

In one embodiment, the detector 20 is a multi-slice detector which includes more than one row of detectors extending in the z-direction, although flat panel or other detector 20 configurations may also be implemented. Depending on the configuration of the detector 20, the x-ray source 12 generates a generally fan, wedge, or cone shaped radiation beam. Moreover, a so-called fourth generation scanner configuration, in which the detector 20 spans an arc of 360 degrees and remains stationary while the x-ray source 12 rotates, may also be implemented.

A patient support 16 such as a couch supports the patient in the examination region 14. The patient support 16 is preferably movable in the z-direction. A controller 28 coordinates the various scan parameters as necessary to carry out a desired scan protocol. In a helical scan, movement of the support 16 and the gantry 18 are coordinated along with such that the x-ray source 12 and the detectors 20 traverse a generally helical path with respect to the patient. In an axial scan, the position of the support 16 remains constant while the source and detector rotate about the patient. The x-ray source parameters such as x-ray tube voltage and current are likewise maintained at values appropriate for a desired protocol.

Data collected by the detector 20 is processed by a reconstructor 22 to generate volumetric data indicative of the interior anatomy of the patient. As is conventional in the CT art, the radiation attenuation at each of a plurality of voxels is expressed in terms of Hounsfield Units or CT numbers.

A general purpose computer serves an operator console 30. The console 30 includes a human readable output device such as a monitor or display and an input device such as a keyboard and mouse. Software resident on the console allows the operator to control the operation of the scanner 10 by establishing desired scan protocols, initiate and terminate scans, view and otherwise manipulate images and other data from the scans, and otherwise interact with the scanner 10. The software, which is implemented by way of computer readable instructions stored on a computer readable medium accessible to the console 30, includes contrast enhanced imaging software 32 such as the Bolus Pro package which is executed by one or more computer processors associated with the console 30. For the purposes of testing, the console 30 also includes software which emulates inputs provided by a human operator and causes the contrast enhanced imaging software 32 to repeatedly conduct a number of simulated contrast enhanced imaging examinations.

An injector interface 34 ordinarily provides an interface between the scanner 10 and a contrast injector. The scanner 10 uses the interface 34 to trigger one or more contrast injections in coordination with a scan of the patient. Alternately, the contrast injector may use the interface 34 to signal that an injection has occurred, with the scanner 10 initiating a scan after a desired delay.

As shown in FIG. 1, however, an adjustable phantom 36 is removably disposed on the patient support 16 and electrically connected to the injector interface 34.

Turning now to FIG. 2, the adjustable phantom 36 includes a base 202, actuator 204, a mechanical linkage such as a link 206 and push arm 208, phantom 210, and a controller 212. With reference to FIG. 4, a shroud 402 is mounted to the base 202 to cover and constrain the motion of the phantom 210, the shroud being omitted from FIG. 2 for the sake of clarity. A suitable cover or covers, again omitted for the sake of clarity, cover the actuator 204, linkage, and controller 212.

The base 202 is configured to be placed on the patient support 16. The base 202 includes a longitudinal axis which is depicted in FIG. 1 to be generally parallel to the longitudinal axis of the scanner 10. Depending on the configuration of the patient support 16, the base may also include suitable provisions for securing the adjustable phantom 36 to the support 16.

The controller 212 and actuator 204 are mounted to the base 202. In one embodiment, the actuator 204 is implemented as a servomotor having an output shaft which rotates about an axis of rotation 230. Of course, other suitable actuators and actuator technologies can be used. For example, a linear actuator may be used. In magnetic resonance applications where the presence of ferrous materials in the imaging region is undesirable, it may be desirable to implement a remotely mounted pneumatic actuator and controller.

The controller 212 receives one or both of a trigger input signal from the injector interface 34 and a user initiated trigger signal. The user initiated trigger signal may be provided by way of a switch which communicates with the controller 212 via wires, radio frequency or infrared signals, or other suitable techniques. The trigger inputs are preferably isolated, for example using an optoisolator.

The controller 212 also preferably includes inputs which allow the adjustment of one or more operating parameters. For example, it may be desirable to adjust the time delay from receipt of a trigger signal to initiating motion, the speed of the actuator 204, the time delay for return of the actuator 204 to a home position, and one or more desired motion profiles. In one embodiment, the parameters are adjusted by way one or more adjustable phantom 36 mounted potentiometers, although other phantom mounted or remote switches, keypads and displays, or the like can also be used. In another implementation, it may be desirable to receive or send configuration information and/or trigger signals via the injector interface 34 so as to mimic communications with an injector. The controller 212 is preferably implemented by way of a microcontroller, analog or digital electronics, or a combination thereof.

In any case, the controller 212 causes movement of the actuator 204 and thus the phantom 210 according to a desired motion profile.

The link 206 and push arm 208 connect the output of the actuator 204 and the phantom 210, which is mounted for longitudinal motion with respect to the base 202. Other linkage arrangements are also contemplated depending on the configuration of a particular actuator 204 and adjustable phantom 36. For example, a linear actuator might employ a suitable jackscrew, while a pneumatic actuator would typically include suitable tubing.

The contrast presented by the phantom 210 varies as a function of position along the direction of motion. With reference to FIGS. 2 and 3a, in one embodiment, the phantom 210 includes a first region 302, a second region 304, and a third or transition region 306. The first 302 and second 304 regions each present a transverse cross section having a substantially constant contrast value. In an embodiment particularly well suited for simulating a CT angiography scan, the first region 302 presents a CT number which approximates that of unenhanced blood, for example in the range of about 40 to 50. The second region 304 presents a CT number which approximates the enhancement following a typical contrast injection, for example in the range of about 200 or higher (trigger levels for contrast enhanced studies typically being established at about 100 to 150). In the transition region 306, the cross section includes both the first and second CT numbers. As illustrated, the phantom 210 has a length of approximately 8 inches (20.32 cm), a width of approximately 3 to 4 inches (7.62 cm to 10.16 cm), and a height of approximately 3 to 4 inches (7.62 cm to 10.16 cm). The first 302 and second 304 regions each have a length of approximately 2 inches (5.08 cm), and the third region has a length of approximately 4 inches (10.16 cm). The angles 305, 307 are approximately 45 degrees. The above contrast values and dimensions are exemplary; other contrast values and dimensions can be selected based on the needs of a particular application. One or both of the first 302 and second 304 regions may also be omitted. A marking 211 of the phantom 210 facilitates placement of the device in a known position on the support 16.

As illustrated in FIGS. 2 and 3a, in the transition region 306, the portion of the cross section having the first and second CT numbers varies as a linear function of longitudinal position. Near the boundary between the first region 302 and the transition region 306, the cross section contains mainly material having the first CT number. Near the boundary between the second region 304 and the transition regions 306, the cross section contains mainly material having the second CT number. At the midpoint of the transition region 306, and with reference to FIG. 4, the ratio of the cross section portion containing material having the first CT number to the cross section portion containing material having the second CT number is approximately equal or 1:1. Non-linear functions may also be implemented. One of the first 210a and second 210b portions may also be omitted in applications where the desired contrast is in the range of the contrast presented by air.

In one embodiment, the first 210a and second 210b portions of the phantom 210 are fabricated from solid plastic having a desired radiation attenuation. Readily available materials include a polyamide polymer such as nylon (which has a CT number of approximately 96) and Acetal GF (which has a CT number of approximately 625). In another embodiment, the blocks may be fabricated from polymer resin which includes a radiation attenuative filler material. Other suitable materials may also be used. The two portions 210a, 210b are fastened together using a suitable adhesive or mechanical fasteners. To facilitate replacement of one of the first 210a and second 210b portions with material having a different contrast characteristic, the portions may be removably attached.

Figure 3B:
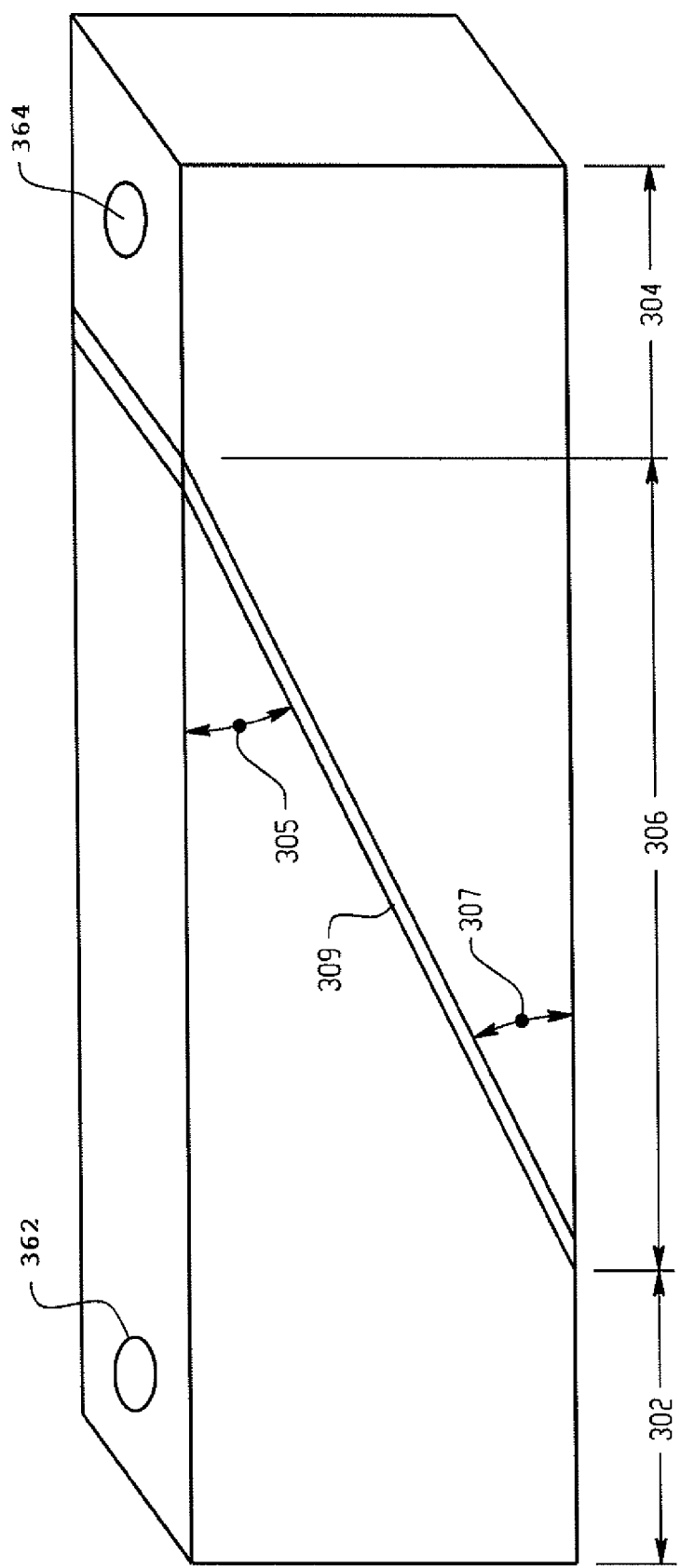

In another embodiment, and with reference to FIGS. 2 and 3b, the phantom 210 is fabricated as a container having first 210a and second 210b regions or chambers separated by a divider 309. Contrast material having the desired contrast is added to the regions 210a, 210b via respective ports or plugs 362, 364. In a CT implementation, for example, the chambers can be filled with varying concentrations of a contrast agent such as iothalamate meglumine mixed in water. As the phantom 210 contains a liquid, the chambers should be liquid tight to prevent leakage or infiltration. The ports 362, 364 may be threaded or otherwise removable to allow the contrast materials to be removed or replaced with contrast material having different CT numbers. The ports 362, 364 are preferably located near the ends of the phantom 210 in the first 302 and second 304 regions. The shroud 402 is fabricated to accommodate placement of the plugs 362, 364, if used. Although shown on a top surface of the phantom 210, the ports may also be located on the sides, ends, or bottom. The ports should include an o-ring or other suitable seals, polytetrafluoroethylene (PTFE) tape, or the like to ensure a liquid tight seal. The walls of the container can be fabricated from clear, 0.25 inch (0.635 cm) thick acrylic (polymethyl methacrylate) plastic, with the divider 309 fabricated from 0.0625 inch (0.159 cm) thick acrylic plastic. The various pieces are joined using a suitable cement. Of course, other construction materials and techniques may be used.

Figure 3C:
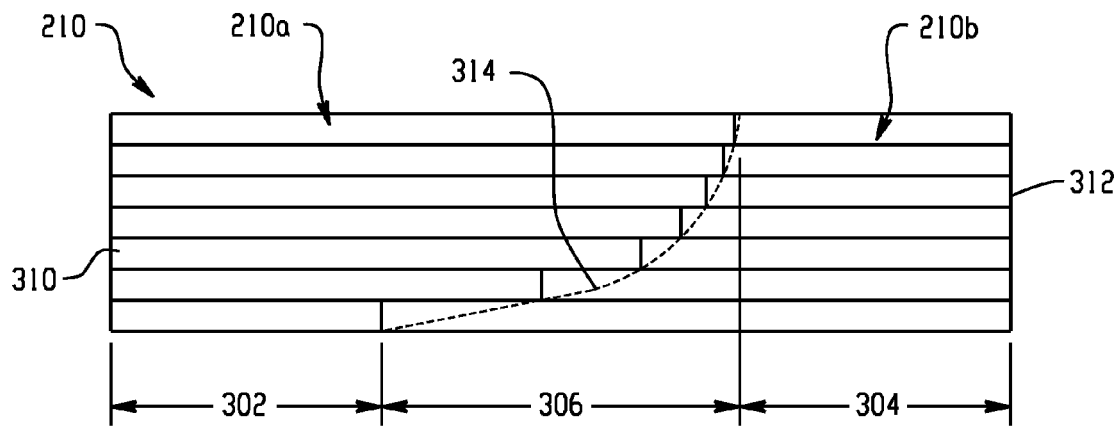

In still another embodiment, and with reference to FIG. 3c, the phantom 210 is fabricated from two or more transversely layered sheets or blocks, A first set of sheets or blocks 310 having a first CT number is disposed in the first region 210a; second set of sheets or blocks 312 having the second CT number is disposed in the second region 210b. FIG. 3c depicts an arrangement in which the lengths of the various sheets or blocks 310, 312 are varied so that the portion of the cross section having the first and second CT numbers varies as a non-linear function of longitudinal position. As depicted by the dashed line 314, the ends of the respective sheets or blocks 310, 312 can be shaped or chamfered to reduce or eliminate the stair step effect, if so desired.

Figure 3D:

In still another embodiment, and with reference to FIG. 3d, the phantom 210 is fabricated from two or more longitudinally layered sheets or blocks 340. The material of each block is selected so that each block has a unique CT number or so that the CT number of the blocks 340 otherwise varies as a desired function of the longitudinal position. Such an arrangement can advantageously be used where measurement of particular CT numbers is required; the motion profile provided by the controller 212 can also be programmed so that the CT number presented at a particular longitudinal position has a known value as a function of time. Where the phantom is used to simulate a contrast enhanced CT scan, the phantom 210 includes a layer which approximates the CT value of unenhanced material and a layer which approximates the CT value of enhanced material. The phantom 210 may also include layers which have CT numbers therebetween.

With reference to FIG. 5, the adjustable phantom 36 can be used to simulate or test the operation of the contrast enhanced imaging software 32 in connection with a CT angiographic examination. At 502, the adjustable phantom 36 is positioned on the support 16, preferably so that the longitudinal motion of the phantom 210 is generally aligned with the longitudinal or z-axis of the scanner 10 and with the longitudinal marking 211 placed at a desired longitudinal position.

At 504, a surview or pilot scan of the phantom 210 is obtained.

A 505, a tracking can of the phantom 210 is obtained.

At 506, the locations and desired enhancement or trigger levels at one or more tracking ROIs are established.

At 508, the support 16 is moved so that the phantom 210 is positioned for the tracking scan, preferably so that the tracking scan is initiated at the longitudinal position indicated by the marking 211. Positioning is facilitated if the phantom 210 is positioned in a known or home position (e.g., with the phantom 210 retracted).

At 510, and with reference to the timing diagram of FIG. 6, the controller 212 receives a trigger signal at time $t_0$. The status of the tracking scan (e.g., active or inactive) as a function of time is indicated by curve 602; the position the phantom 210 is indicated by curve 604.

At 512 and following a delay which is less than expected transit time for the contrast agent to reach the tracking ROI(s), the tracking scan is initiated time $t_1$. The CT scanner 10 thus obtains a series of relatively lower dose scans to detect the arrival of contrast agent at the tracking ROI(s).

At 514, the controller 212 initiates motion of the phantom 210 at time $t_2$. The delay between receipt of the trigger signal at time $t_0$ and the initiation of motion at time $t_2$ is selected so that the boundary of the transition region 306 reaches the location of the tracking scan following a delay which approximates the arrival of contrast agent following an injection. In practice, the desired delay typically ranges from about zero to ten seconds.

At 516, the controller 212 causes the phantom 210 to move according to a desired motion profile, for example so that the time rate of change of the CT number portions of the phantom 210 at the location of the tracking scan is approximately linear.

At 518, the controller 212 terminates the motion of the phantom 210 at time $t_3$. The delay between times $t_2$ and $t_3$ is preferably selected to approximate the time required to reach peak enhancement following arrival of contrast agent at the tracking ROI(s). In practice, the time desired time interval typically ranges from about two seconds (or as fast at the actuator will move) to about ten seconds.

At 520, the tracking scan is terminated when the measured enhancement value reaches the specified enhancement level, or otherwise at time $t_4$. Depending on the particular test or simulation, a diagnostic scan may also be initiated.

At 522, the controller 212 causes the phantom 210 to return to the home position beginning at time $t_5$, with the phantom 210 reaching the home position at time $t_6$.

At 524, the process is repeated as desired, for example as part of an automated simulation or testing procedure.

FIGS. 7a, 7b, 7c, and 7d depict how exemplary first 702 and second 704 tracking ROIs would appear as the phantom 210 depicted in FIG. 3a or 3b progresses through the plane of the tracking scan in an exemplary contrast enhanced angiographic procedure. The figures present an end view with the motion of the phantom 210 toward the viewer.

Figure 7A:
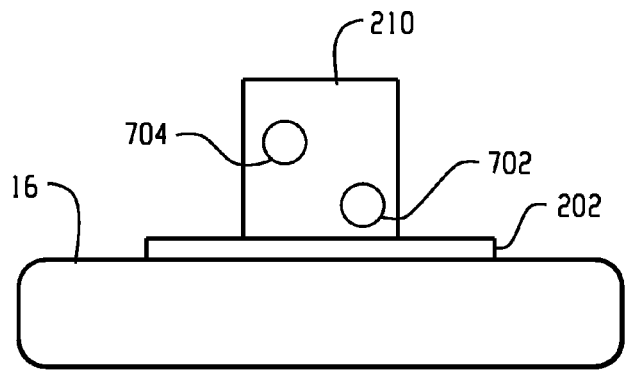

In FIG. 7a, the phantom 210 is positioned so that a tracking scan is obtained in the first region 302 of the phantom 210, for example at the position of the marking 211. Accordingly, the first 702 and second 704 tracking ROIs contain contrast values which approximate unenhanced blood.

Figure 7B:
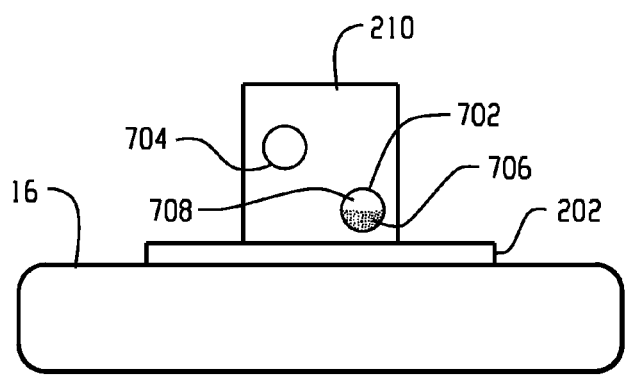

In FIG. 7b, the phantom 210 is positioned so that a tracking scan is obtained in the transition region 306 relatively near the first region 302. Accordingly, a first part of 706 of the first ROI 702 simulates contrast enhanced blood, while a second part 708 simulates unenhanced blood. Where the contrast enhanced imaging software 32 averages the enhancement values in the ROI, such an arrangement is particularly effective for simulating an increase in CT number associated with the arrival of contrast agent. The second tracking ROI 704 contains contrast values which simulate unenhanced blood.

Figure 7C:
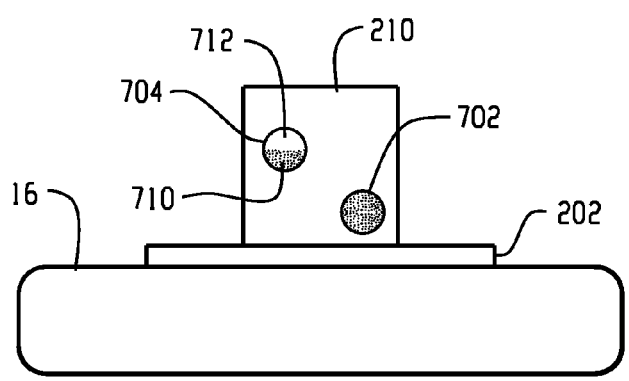

In FIG. 7c, the phantom 210 is positioned so that a tracking scan is obtained in the transition region 306 relatively near the second region 304. The first tracking ROI 702 contains contrast values which simulate enhanced blood. A first part of 710 of the second tracking ROI 704 simulates contrast enhanced blood, while a second part 712 simulates unenhanced blood.

Figure 7D:
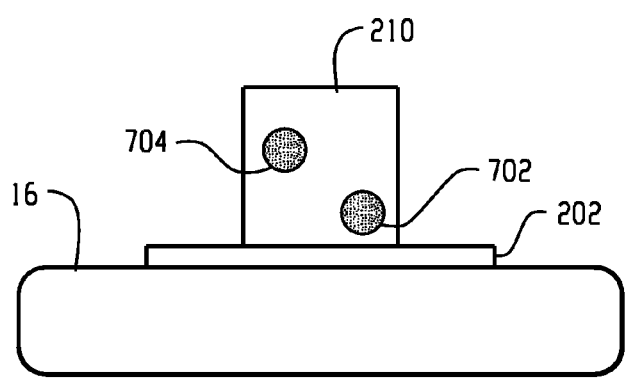

In FIG. 7d, the phantom 210 is positioned so that a tracking scan is obtained in the second region 304 of the phantom 210. Accordingly, the first 702 and second 704 tracking ROIs contain contrast values which approximate enhanced blood.

Other variations are also possible. For example, the adjustable phantom 36 may be battery powered with provisions to receive power from the power mains or other external source. Various configurations of the phantom 210 are also contemplated. For example, the direction of the transition region "wedge" may be implemented as depicted by the dashed line 333 in FIG. 3a. If desired, functionality equivalent to that described above can be obtained by switching the contrast values of the first 210a and second 210b regions and considering the home position to be the extended position. Similarly, the contrast block can be visualized as being flipped on its side so that the wedge of the transition region 306 is formed from side to side. If desired, the positions of the tracking ROI(s) can be adjusted accordingly. It is also not necessary that the phantom 210 have a rectangular cross section. To provide a still more realistic simulation, the phantom 210 may also be embedded in a more anthropomorphic phantom. Indeed, the phantom 210 may also be used to simulate a diagnostic scan following the tracking scan, with the controller 212 configured to provide the desired motion profile.

While described above primarily in relation to x-ray computed tomography, the phantom may used in other applications such as magnetic resonance, positron emission tomography, single photon emission computed tomography, x-ray imaging, and the like through the use of suitable materials and contrast agents. The phantom may also be used in applications other than simulating contrast angiography.

Of course, modifications and alterations will occur to others upon reading and understanding the preceding description. It is intended that the invention be construed as including all such modifications and alterations insofar as they come within the scope of the appended claims or the equivalents thereof.

The invention claimed is:

1. An apparatus comprising:
   a base adapted to be placed on an object support of a scanner which generates information indicative of a physical characteristic of an interior of an object under examination;
   a phantom carried by and movable with respect to the base in a direction of motion, wherein the phantom includes a first chamber for receiving a contrast material and a physical characteristic of the phantom varies along the direction of motion; and
   an actuator which causes the phantom to move with respect to the base in the direction of motion.

2. The apparatus of claim 1 wherein the scanner includes a CT scanner and the physical characteristic is radiation attenuation.

3. The apparatus of claim 1 wherein the direction of motion is linear.

4. The apparatus of claim 1 wherein the phantom includes a cross section which is transverse to the direction of motion and wherein a transverse cross section includes a first cross section portion in which the physical characteristic has a first value and a second cross section portion in which the physical characteristic has a second value, and wherein the ratio of the first cross section portion to the second cross section portion varies along the direction of motion.

5. The apparatus of claim 4 wherein the ratio varies linearly along the direction of motion.

6. The apparatus of claim 4 wherein the phantom includes a region in which the ratio is zero.

7. The apparatus of claim 1 wherein the phantom includes a cross section which is transverse to the direction of motion and wherein a transverse cross section includes a first cross section portion in which the physical characteristic has a first value, which simulates unenhanced blood, and a second cross section portion in which the physical characteristic has a second value, which simulates contrast enhanced blood, and wherein a ratio of the first cross section portion to the second cross section portion varies along the direction of motion.

8. The apparatus of claim 1 wherein the base comprises a securing mechanism for securing the base to the object support.

9. The material of claim 1 wherein the first chamber includes a transverse cross section and wherein the area of the transverse cross section varies along the direction of motion.

10. The apparatus of claim 9 wherein the phantom includes a second chamber for containing a contrast material.

11. The apparatus of claim 10 wherein the first and second chambers are separated by a divider, and wherein the divider is disposed at an angle oblique to the direction of motion.

12. The apparatus of claim 1 wherein the phantom includes first and second longitudinally disposed material layers, and wherein the first and second material layers have different physical characteristic values.

13. The apparatus of claim wherein the phantom includes a plurality of transverse material layers.

14. The apparatus of claim 1 wherein the actuator causes the phantom to move with respect to the base in the direction of motion, which simulates a change in the physical characteristic in a region of interest resulting from the introduction of contrast agent into a living subject.

15. The apparatus of claim 1 wherein the actuator causes the phantom to move with respect to the base in the direction of motion that simulates the arrival of contrast enhanced blood following a contrast agent injection.

16. The apparatus of claim 1 including a controller adapted to receive a trigger signal from a contrast injector interface and to cause a motion of the actuator in response to the trigger signal.

17. A method comprising:
positioning a phantom with respect to an object support of a medical imaging scanner, which scanner generates information indicative of a physical characteristic of an interior of an object under examination;
using an actuator to move the phantom relative to the object support so as to change a value of a physical characteristic in a region of interest, wherein the value of the physical characteristic changes linearly with time;
scanning the region of interest;
repeating the step of scanning a plurality of times during movement of the phantom; and
using information from the scans to determine the value of the physical characteristic in the region of interest at a plurality of times.

18. The method of claim 17 wherein the physical characteristic is radiation attenuation.

19. The method of claim 17 wherein the change in the value of the physical characteristic simulates an arrival of contrast enhanced blood during a contrast enhanced angiography scan.

20. The method of claim 17 wherein the phantom includes a cross section which is transverse to the direction of motion and wherein a transverse cross section includes a first cross section portion in which the physical characteristic has a first value and a second cross section portion in which the physical characteristic has a second value, and wherein a ratio of the first cross section portion to the second cross section portion varies along the direction of motion.

21. The method of claim 17 wherein the step of using an actuator includes moving the phantom in a direction of motion, wherein the phantom includes a first portion wherein the physical characteristic has a first value and a second portion wherein the physical characteristic has a second value, and wherein a boundary between the first and second portions is oblique to the direction of motion.

22. The method of claim 17 wherein the step of using an actuator includes moving the phantom in a direction of motion, wherein the phantom includes a chamber for receiving a contrast material, and wherein the transverse cross section of the chamber varies along the direction of motion.

23. The method of claim 17 wherein the phantom includes a plurality of transversely disposed material layers.

24. The method of claim 17 wherein the phantom includes a plurality of longitudinally disposed material layers.

25. The method of claim 17 including determining a time at which the value of the physical characteristic reaches a threshold value.

26. The method of claim 17 including using the actuator to move the phantom to a home position and repeating the steps of using the actuator to move the phantom relative to the object support, scanning the region of interest, repeating the step of scanning a plurality of times, and using the information from the scans a plurality of times.

27. An apparatus comprising:
a base;
a phantom carried by and movable with respect to the base in a direction of motion, wherein the phantom includes a first portion in which a physical characteristic of the phantom has a first value, a second portion in which the physical characteristic of the phantom has a second value, and a boundary between the first and second portions, and the boundary is oblique to the direction of motion; and
an actuator which causes the phantom to move with respect to the base in the direction of motion so as to vary the value of the physical characteristic in a region of interest.

28. The apparatus of claim 27 wherein the phantom includes a first chamber adapted to receive a contrast material and which first chamber defines the first portion and a second chamber adapted to receive a contrast material and which second chamber defines the second portion.

29. The apparatus of claim 27 wherein the base is configured to be placed in an imaging examination region.

30. The apparatus of claim 27 including a controller which initiates motion of the actuator in response to an input signal.

* * * * *